United States Patent
Ito et al.

(10) Patent No.: US 7,648,487 B2
(45) Date of Patent: Jan. 19, 2010

(54) SYRINGE

(75) Inventors: Akira Ito, Osaka (JP); Yoshihisa Murai, Osaka (JP); Takeshi Nizuka, Osaka (JP); Shin-ich Kawamura, Osaka (JP); Dai Sutou, Osaka (JP)

(73) Assignee: Nipro Corporation, Osaka (JP)

( * ) Notice: Subject to any disclaimer, the term of this patent is extended or adjusted under 35 U.S.C. 154(b) by 617 days.

(21) Appl. No.: 11/236,662

(22) Filed: Sep. 28, 2005

(65) Prior Publication Data

US 2006/0200084 A1  Sep. 7, 2006

(30) Foreign Application Priority Data

Sep. 28, 2004 (JP) ............... 2004-281164
Dec. 28, 2004 (JP) ............... 2004-379821

(51) Int. Cl.
*A61M 5/315* (2006.01)

(52) U.S. Cl. .................................... 604/230

(58) Field of Classification Search ............... 604/191, 604/230, 218, 187, 265, 12, 221; 523/210; 508/136, 208
See application file for complete search history.

(56) References Cited

U.S. PATENT DOCUMENTS

| 4,500,310 A | * | 2/1985 | Christinger | 604/228 |
|---|---|---|---|---|
| 4,781,676 A | * | 11/1988 | Schweighardt et al. | 604/21 |
| 5,186,972 A | | 2/1993 | Williams et al. | |
| 5,236,606 A | * | 8/1993 | Rangel | 508/161 |
| 5,352,378 A | | 10/1994 | Mathisen et al. | |
| 5,605,957 A | * | 2/1997 | Yoshida | 516/100 |
| 6,015,777 A | | 1/2000 | Lostritto, Jr. et al. | |
| 6,200,627 B1 | | 3/2001 | Lubrecht | 427/28 |
| 6,243,938 B1 | | 6/2001 | Lubrecht | 29/458 |
| 6,746,430 B2 | | 6/2004 | Lubrecht | 604/230 |
| 7,141,042 B2 | | 11/2006 | Lubrecht | 604/230 |
| 2001/0002434 A1 | | 5/2001 | Lubrecht | 604/232 |
| 2001/0039400 A1 | | 11/2001 | Lubrecht | 604/193 |
| 2002/0069616 A1 | | 6/2002 | Odell et al. | |
| 2003/0023143 A1 | | 1/2003 | Abe et al. | |
| 2005/0170071 A1 | * | 8/2005 | Eramo | 427/2.1 |

FOREIGN PATENT DOCUMENTS

| EP | 0 277 603 A | 8/1988 |
|---|---|---|
| EP | 0 284 340 A | 9/1988 |
| EP | 0 546 237 A | 6/1993 |
| JP | 5-131029 A | 5/1993 |
| JP | 2001-289326 A | 10/2001 |
| JP | 2002-506694 A | 3/2002 |
| JP | 2002-172166 A | 6/2002 |
| JP | 2004-57819 A | 2/2004 |
| JP | 2004-162761 A | 6/2004 |

* cited by examiner

*Primary Examiner*—Nicholas D Lucchesi
*Assistant Examiner*—Jenner Yeh
(74) *Attorney, Agent, or Firm*—Kubovcik & Kubovcik

(57) ABSTRACT

A syringe coated with a lubricant containing a silicone oil and a fine silica powder on the inner surface of the barrel of the syringe can be used for injection of a surface-active drug solution without oil droplet formation on the inner surface while preventing an increase of the gasket sliding friction.

8 Claims, No Drawings

SYRINGE

FIELD OF THE INVENTION

The present invention relates to a syringe and medical lubricant, more specifically to a syringe for injection of a drug solution having a surface activity and to a prefilled syringe filled with a drug solution having a surface activity.

BACKGROUND OF THE INVENTION

Syringes are one of medical devices that need lubricants for smooth sliding of the components. Disposable syringes made from a synthetic resin, as syringes used for general use, comprise a barrel, a gasket in tight contact with an inner surface of the barrel, and a plunger extending from the gasket towered the rear end of the syringe to slide the gasket. The syringes are used with the following method: the plunger is moved to the direction of the rear end of the barrel to fill the syringe with a drug solution, and the plunger is moved toward the tip of the barrel to discharge the drug solution charged in the syringe from the tip. Also, prefilled syringes, which are filled with drug solutions beforehand, are used with the following method: a plunger is moved toward the tip of a barrel to discharge the drug solution contained in the syringe.

The gasket used for these syringes is in tight contact with the inner surface of the barrel. The gasket is used to discharge the drug solution from the barrel while preventing leakage of the drug solution charged in the syringe and mixing of air bubbles, and is formed from an elastic material such as a synthetic rubber. The gasket has to slide in the barrel smoothly to discharge the drug solution, whereby in conventional disposable syringes, a silicone oil is applied as a lubricant to the inner surface of the barrel or the outer surface of the gasket.

However, the syringes are disadvantageous in that, when they are used for injection of a drug solution containing a drug having a surface activity, the silicone oil applied as a lubricant forms oil droplets on the inner surface of the barrel or the sliding friction of the gasket is. increased, whereby there has been a demand for a measure therefor. The generation of the oil droplets on the inner surface of the syringe is a problem to be solved in particular, because there is a possibility that the oil droplets mixed with the drug solution by separating from the inner surface of the syringe will be injected into a human body.

In regard to the problem caused by the contacting lubricant applied to the inner surface of the barrel or the outer surface of the gasket and the drug solution contained in the syringe, syringes with which the measures for solving the problem are heretofore known as follows: syringes having such a structure that a lubricant is blended with a material of a gasket and not applied to surfaces of the syringe or gasket (e.g., Patent Documents 1 and 2); syringes having such a shape that a gasket does not directly come into contact with a drug solution (e.g., Patent Document 3); syringes using a particular method for fixing a lubricant to a gasket, thereby making the lubricant less likely to fall off (e.g., Patent Documents 4 and 5); and syringes having such a structure that a lubricant is applied only to a necessary portion of the syringe to reduce a contact area between the lubricant and a drug solution (e.g., Patent Document 6).

However, these technologies require a drastic design change of structures from the conventional syringes or require only a small design change with insufficient effects. These technologies are not sufficient as a measure for using the syringes for injection of a surface-active drug solution without the problem, which is one of the applications of the syringes.

Patent Document 1:
    Japanese publication Number Hei5-131029

Patent Document 2:
    Japanese publication Number 2001-289326

Patent Document 3:
    Japanese publication Number 2002-172166

Patent Document 4:
    Japanese publication Number 2002-506694

Patent Document 5:
    Japanese publication Number 2004-162761

Patent Document 6:
    Japanese publication Number 2004-57819

Accordingly, an object of the present invention is to provide a syringe which can be designed and produced in the same manner as conventional syringes without a drastic design change, and can be used for injection of a drug solution having a surface activity without generation of oil droplets on the inner surface of the syringe and an increase of the sliding friction of the gasket.

SUMMARY OF THE INVENTION

As a result of intense study, the inventors have found that, by using a silicone oil containing a fine silica powder as a lubricant, generation of oil droplets on an inner surface of a syringe can be prevented at points of contact between the lubricant and a drug solution having a surface activity. The present invention has been accomplished by the finding. Further, by preventing the generation of the droplets on the inner surface of the syringe, an increase of the sliding friction of the gasket can be reduced.

In this invention, in the case that the lubricant for the medical use comprises a straight silicone oil as a main component, a fine silica powder, and 0.1 to 15% by weight of a nonionic surfactant, the lubricant is not suspended as oil droplets in the drug solution having surface activity by separation due to the surface activity of the drug solution with shaking of the syringe. Therefore, the visibility of the drug solution is not deteriorated, and the syringe is not deteriorated in appearance for medical use.

The present invention is also a lubricant for medical use, which comprises a straight silicone oil as a main component, a fine micronized silica powder, and a nonionic surfactant, the lubricant being characterized in that the lubricant contains 5 to 20% by weight of the micronized silica and 0.1 to 15% by weight of the nonionic surfactant. In the case that said syringe contains a drug solution having surface activity therein, when the syringe is used with said lubricant, the lubricant is not suspended as oil droplets in the drug solution having surface activity by separation due to the surface activity of the drug solution with shaking of the syringe. Therefore, the visibility of the drug solution is not deteriorated, and the syringe is not deteriorated in appearance for medical use.

Thus, the invention relates to a syringe comprising a barrel, a gasket contacting tightly with an inner surface of the barrel, and a plunger extending from the gasket to the rear end of the syringe to slide the gasket, wherein the inner surface of the barrel is coated with a lubricant containing a silicone oil and a fine silica powder.

By improving the lubricant used in conventional syringes, the syringe of the present invention forms no oil droplets even in the case of using a specific drug solution and prevents an increase of the gasket sliding friction due to the oil droplets. Therefor, the syringe can be used without the selection of suitable drug solutions. Further, since the invention is related to the improvement of the lubricant as above, the invention can be applied to the conventional syringes without making a significant change to the conventional production processes.

Furthermore, the syringe of the invention may be a prefilled syringe which is filled with the drug solution beforehand. Also the prefilled syringe can be used without the selection of suitable drug solutions filled within the syringe before head, and can be used while preventing the generation of the oil droplets and an increase of the gasket sliding friction.

DESCRIPTION OF THE PREFERRED EMBODIMENTS

The syringe of the present invention may have a structure essentially the same as the conventional syringes. The structure of the syringe comprises a barrel with open ends, a gasket in tight contact with an inner surface of the barrel, and a plunger for sliding the gasket. The plunger is disposed in the barrel such that the tip is fixed to the gasket and the rear end constantly protrudes from the rear end of the barrel. By moving the plunger backward and forward, the gasket slides in the barrel, a drug solution is aspirated from the open tip end into the barrel. The drug solution contained in the barrel is discharged and injected into a patient. A prefilled syringe, in which the barrel is filled with the drug solution beforehand, is also within the scope of the invention.

In the syringe of the invention, the gasket slides backward and forward while keeping tight contact with the inner surface of the barrel, and a lubricant containing a silicone oil and a fine silica powder is applied to the inner surface of the barrel to reduce the sliding friction.

(Silicone Oil)

As the silicone oil contained in the lubricant used in the invention, polydimethylsiloxane is generally used. Polydimethylsiloxane having substituents in the side chains and ends thereof can be used without the lubricity being deteriorated in the lubricant. For example, polymethylphenylsiloxane, polymethylhydrogensiloxane and the like can be exemplified.

The viscosity at 25° C. of the silicone oil is preferably 100 to 1,000,000 c St, and more preferably 1,000 to 100,000 c St. A silicone oil having a viscosity of less than 100 c St is likely to separate from the inner surface of the barrel to be suspended in the drug solution. A silicone oil having a viscosity of more than 1,000,000 c St is poor in lubricity and likely to increase the sliding friction of the gasket.

A straight silicone oil is preferably used for the silicone oil, since the lubricant is not suspended as oil droplets in the drug solution having surface activity by the separation due to the surface activity of the drug solution in the case that the syringe with the lubricant is shaken. The straight silicone oil is a silicone oil other than modified silicone oils, and in which a methyl group, a phenyl group, or a hydrogen atom is attached thereto as a substituent. The lubricant of the invention contains 50% by weight or more of the straight silicone oil as the main component. Specific examples of the straight silicone oil include polydimethylsiloxane, polymethylphenylsiloxane, polydiphenylsiloxane, polymethylhydrogensiloxane, etc.

(Fine Silica Powder)

The lubricant used in the invention is described in more detail below. The lubricant used in the invention contains 0.1 to 20% by weight, and more preferably 1 to 10% by weight of a fine silica powder. When the amount of the fine silica powder contained is less than 0.1% by weight, the lubricant comes into contact with the drug solution containing the surface-active drug to form oil droplets on the surface of the syringe, and thereby increases the sliding friction of the gasket. Further, when the amount of the fine silica powder contained is more than 20% by weight, the lubricant has a too high viscosity and may not have sufficient ability of reducing the sliding friction of the gasket.

The fine silica powder contained in the lubricant used in the invention may be a wet silica or dry silica. Specific examples of the fine silica powders include precipitated silicas, silica xerogels, fumed silicas, and ones prepared by treating surfaces of these silicas with an organic silyl group. The specific surface area of the fine silica powder used in the invention, measured by a BET method, is preferably 100 $m^2/g$ or more, and more preferably 150 $m^2/g$ or more. When the specific surface area of the micronized silica is 100 $m^2/g$ or more, dispersing the silica powder in the lubricant uniformly becomes easier.

The syringe of the invention is characterized by using the lubricant containing the silicone oil and the fine silica powder. The lubricant is effective for use of the syringe in injection of a drug solution containing the drug having a surface activity. When the drug solution is injected by the syringe, the lubricant applied to the inner surface of the barrel in the syringe comes into contact with the drug solution charged in the barrel. The conventional lubricant composed of only the silicone oil, which has been used in syringes, is disadvantageous in that, in the case of using a drug solution containing the surface-active drug, the lubricant forms oil droplets to increase the sliding friction of the gasket. However, by using the lubricant prepared by combining the fine silica powder with the silicone oil in the invention, the lubricant forms no oil droplets on the surface, and thereby can prevent an increase of the sliding friction of the gasket, even in the case of using the drug solution containing the surface-active drug.

When the fine silica powder is used with a nonionic surfactant in the syringe containing a surface active drug solution, it is preferably that the fine silica powder has a number average particle size of 10 μm or less.

The content of the fine silica powder contained in the medical lubricant of the invention is 5 to 20% by weight, and more preferably 10 to 15% by weight, when the silica powder is used with a nonionic surfactant in the syringe containing a surface active drug solution. When the content of the fine silica powder is less than 5% by weight, the lubricant has a small yield value, and the lubricant is likely to fall off and be suspended as oil droplets in the drug solution. On the other hand, when the content of the fine silica powder is more than 20% by weight, the lubricant has a higher viscosity. Therefore, in the case that a member is applied with the lubricant containing the fine silica powder which is more than 20% by weight, sliding friction of the member may not be sufficiently reduced.

(Nonionic Surfactant)

The nonionic surfactant contained in the medical lubricant of the invention is a surfactant that is not ionized in water, and specific examples thereof include polyoxyethylene higher alcohol ethers, polyoxyethylene alkyl phenyl ethers, sorbitan alkylates, polyoxyethylene sorbitan alkylates, glycerolalkylates, polyoxyethylene hardened caster oils, silicone-based nonionic surfactants having hydrophilic substituents, and the like. Among them, preferred as the nonionic surfactants in the invention are polyoxyethylene sorbitan monooleate, polyoxyethylene hardened caster oils, and polyether-modified silicones, and the like.

In the medical lubricant of the invention, the content of the nonionic surfactant blended is 0.1 to 15% by weight, and more preferably 0.5 to 5% by weight. When the content of the nonionic surfactant is less than 0.1% by weight or more than 15% by weight, it is likely that part of the lubricant separates and is suspended in a drug solution.

(Other Additives)

The lubricant may contain components other than the silicone oil and the fine silica powder as long as the components do not deteriorate the effect of preventing the formation of oil droplets during contacting of the lubricant with the drug solution containing the surface-active drug.

(Production Method)

The lubricant according to the invention may be obtained by mixing the components homogeneously using a mixing apparatus such as a homo mixer, a colloid mill, a three-roll mill, or the like. The obtained lubricant is applied to the inner surface of the barrel of the syringe, and the application method used may be a known technology such as a transfer method, a spray method, and the like.

(Drug Solution Having Surface Activity)

The drug having surface activity is a drug having a surface tension of 70 mN/m or less, such as a hyaluronate salt, a glycyrrhizinate salt, a polyoxyethylene sorbitan ester, polyethylene glycol, polyoxyethylene castor oil, polypropylene glycol, lecithin, and glycerin. These surface-active drugs come into contact with the silicone oil to affect the fluidity of the silicone oil, thereby forming the oil droplets at the interface between the silicone oil and the drug. Although, the mechanism of forming the oil droplets is currently unexplained, it has been found that by the use of the lubricant according to the invention containing the fine silica powder blended with the silicone oil, the mechanism relating to the formation of the oil droplets is prevented from proceeding, thereby preventing an increase of the gasket sliding friction.

The drug solution may contain any one of the above mentioned surface-active drugs, or two or more kinds of drugs selected from the above mentioned surface-active drugs. There are no particular limitations on the components other than the drug in the drug solution.

(Lubricant)

The lubricant in the invention can be used by applying with a syringe. It is preferable that the lubricant is used for a syringe containing a surface active drug solution therein since the lubricant does not react with the drug solution. When the drug solution is infused by using the syringe, the lubricant applied to the inner surface of the outer cylinder in the syringe comes into contact with the drug solution charged in the outer cylinder. When syringes coated with a conventional lubricant composed only of silicone oil are used for injection of a drug solution containing a surface-active drug, oil droplets may be formed in the lubricant to increase sliding friction of a gasket. Further, when the lubricant is suspended as oil droplets in the drug solution by separation, the visibility of the drug solution is deteriorated. The syringe is poor in appearance for medical use.

However, by using the lubricant of the invention, even in the case of using a drug solution containing the surface-active drug, the lubricant forms no oil droplets on the surface. The lubricant is not suspended in the drug solution, whereby there is provided a syringe free from the possibility of an increase of the sliding friction of the gasket.

The medical lubricant of the invention has the above effects. Therefore, it can be preferably used not only for common syringes but also for a prefilled syringe that is filled beforehand with a drug solution containing a surface-active drug.

The drug having a surface activity is a drug having a surface tension of 70 mN/m or less, such as a hyaluronate salt, a glycyrrhizinate salt, a polyoxyethylene sorbitan ester, polyethylene glycol, polyoxyethylene castor oil, polypropylene glycol, lecithin, and glycerin.

Such surface-active drugs affect the fluidity of a silicone oil by contact with the silicone oil. Such surface-active drugs cause formation of form the oil droplets at the interface between the silicone oil and the drug, and cause separation of a part of the silicone oil. The mechanism has not been elucidated.

However, it has been found that the medical lubricant according to the invention comprising the straight silicone oil containing the fine silica powder and the nonionic surfactant has effects of inhibiting the mechanism of formation of the oil droplets to prevent the formation. The lubricant also prevents an increase of the gasket sliding friction and the separation of part of the silicone oil.

The drug solution may contain any one of the above surface-active drugs, or two or more of the drugs. There are no particular limitations on the components other than the drug in the drug solution.

(Lubricant for Medical Use)

It is preferable that the lubricant for the medical use in the present invention is used for the devices whose component(s) slide smoothly such as injection needles, catheters, and guide wires and the like, as well as syringes. Since the lubricant has the above mentioned effects, the lubricant is more preferably used for the medical devices using a drug solution containing a drug having surface activity.

EXAMPLES

The present invention will be described more specifically with reference to Examples below, but the present intention is not limited to these examples.

Example 1

To 99.9 parts by weight of a polydimethylsiloxane ("DC360" available from Dow Corning Silicone Co., Ltd., Viscosity at 25° C.: 12,500 c St), 0.1 part by weight of a silica (a fine silica powder, "AEROSIL R976S" available from Nippon Aerosil Co., Ltd., Specific surface area: 240 $m^2$/g) was added. The obtained composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a 20-mL syringe, and the syringe was filled with 20 mL of an injection (HISHIPHAGEN-C injection available from Nipro Pharma Corporation, a monoammonium glycyrrhizinate-containing drug solution, Surface tension: 66 mN/m), and was subjected to high pressure steam sterilization with the gasket closing the barrel. The prefilled syringe of Example 1 was thereby obtained.

Example 2

A prefilled-syringe filled with a HISHIPHAGEN injection solution was obtained in the same manner as Example 1, except for using a lubricant prepared by using 0.5 parts by weight of the silica to 99.5 parts by weight of the polydimethylsiloxane instead of the lubricant of Example 1.

Example 3

A prefilled-syringe filled with a HISHIPHAGEN injection solution was obtained in the same manner as Example 1 except for using a lubricant prepared by using 1 part by weight of the silica to 99 parts by weight of the polydimethylsiloxane instead of the lubricant of Example 1.

Example 4

A prefilled-syringe filled with a HISHIPHAGEN injection solution was obtained in the same manner as Example 1 except for using a lubricant prepared by using 5 parts by weight of the silica as a fine silica powder to 95 parts by weight of the polydimethylsiloxane instead of the lubricant of Example 1.

Example 5

A prefilled-syringe filled with a HISHIPHAGEN injection solution was obtained in the same manner as Example 1 except for using a lubricant prepared by using 10 parts by weight of the silica to 90 parts by weight of the polydimethylsiloxane instead of the lubricant of Example 1.

Example 6

A prefilled-syringe filled with a HISHIPHAGEN injection solution was obtained in the same manner as Example 1 except for using a lubricant prepared by using 20 parts by weight of the silica to 80 parts by weight of the polydimethylsiloxane instead of the lubricant of Example 1.

Example 7

To 95 parts by weight of a polydimethylsiloxane (DC360 available from Dow Corning Silicone Co., Ltd., Viscosity at 25° C.: 100 c St), 5 parts by weight of a silica (AEROSIL R976S available from Nippon Aerosil Co., Ltd., Specific surface area: 240 m$^2$/g) was added. The obtained composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Example 7 was thereby obtained.

Example 8

A prefilled-syringe filled with a HISHIPHAGEN injection was obtained in the same manner as Example 7 except for using a polydimethylsiloxane (KF96 available from Shin-Etsu Chemical Co., Ltd., Viscosity at 25° C.: 1,000,000 c St) instead of the silicone oil of Example 7.

Example 9

To 95 parts by weight of a polydimethylsiloxane (DC360 available from Dow Corning Silicone Co., Ltd., Viscosity at 25° C.: 12,500 c St), 5 parts by weight of a silica (AEROSIL R976S available from Nippon Aerosil Co., Ltd., Specific surface area: 240 m$^2$/g) was added. The obtained composition was mixed by a T. K. HOMO MIXER manufactured by Tokushu Kika Kogyo Kabushiki Kaisha, and a semi-transparent liquid of a lubricant was obtained. 10 mg of the lubricant was applied to an inner surface of a 20-mL syringe, and the syringe was filled with 20 mL of a MINOPHAGEN injection solution (STRONGER NEO-MINOPHAGEN C available from Minophagen Pharmaceutical Company, a monoammonium glycyrrhizinate-containing drug solution, Surface tension: 59.7 mN/m) and was subjected to high pressure steam sterilization with the gasket closing the barrel. The prefilled syringe of Example 9 was thereby obtained.

Example 10

To 95 parts by weight of a polydimethylsiloxane (DC360 available from Dow Corning Silicone Co., Ltd., Viscosity at 25° C.: 12,500 c St), 5 parts by weight of a silica (AEROSIL R976S available from Nippon Aerosil Co., Ltd., Specific surface area: 240 m$^2$/g) was added. The obtained composition was mixed by a T. K. HOMO MIXER manufactured by Tokushu Kika Kogyo Kabushiki Kaisha, and a semi-transparent liquid of a lubricant was obtained. 10 mg of the lubricant was applied to an inner surface of a 20-mL syringe, and the syringe was filled with 20 mL of POLYSORBATE 20 SOLUTION (available from Wako Pure Chemical Industries, Ltd., polyoxyethylene sorbitan monolaurate, a drug solution containing 60 mg/L of polyoxyethylene sorbitan monolaurate, Surface tension: 40.8 mN/m) and was subjected to high pressure steam sterilization with the gasket closing the barrel. The prefilled syringe of Example 10 was thereby obtained.

Example 11

A prefilled-syringe filled with a POLYSORBATE 80 SOLUTION injection was obtained in the same manner as Example 10 except for using POLYSORBATE 80 SOLUTION (available from Wako Pure Chemical Industries, Ltd., polyoxyethylene sorbitan monooleate, a drug solution containing 60 mg/L of polyoxyethylene sorbitan monooleate, Surface tension: 47.5 mN/m) instead of the drug solution of Example 10.

Comparative Example 1

10 mg of polydimethylsiloxane (DC360 available from Dow Corning Silicone Co., Ltd., Viscosity at 25° C.: 12,500 c St) was applied to an inner surface of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m). The syringe was subjected to high pressure steam sterilization with the gasket closing the barrel. The prefilled syringe of Comparative Example 1 was thereby obtained.

Comparative Example 2

A prefilled-syringe filled with a HISHIPHAGEN injection was obtained in the same manner as Comparative Example 1 except for using a polydimethylsiloxane (DC360 available from Dow Corning Silicone Co., Ltd., Viscosity at 25° C.: 100 c St) instead of the silicone oil of Comparative Example 1.

Comparative Example 3

A prefilled-syringe filled with a HISHIPHAGEN injection solution was obtained in the same manner as Comparative Example 1 except for using a silicone oil (KF96 available from Shin-Etsu Chemical Co., Ltd., Viscosity at 25° C.: 1,000,000 c St) instead of the silicone oil of Comparative Example 1.

Comparative Example 4

A prefilled-syringe filled with a MINOPHAGEN injection solution was obtained in the same manner as Comparative Example 1 except for using a MINOPHAGEN (STRONGER NEO-MINOPHAGEN C available from Minophagen Pharmaceutical Company, a monoammonium glycyrrhizinate-containing drug solution, Surface tension: 59.7 mN/m) instead of the drug solution of Comparative Example 1.

Comparative Example 5

A prefilled-syringe filled with a POLYSORBATE 20 SOLUTION was obtained in the same manner as Comparative Example 1 except for using POLYSORBATE 20 SOLUTION (available from Wako Pure Chemical Industries, Ltd., polyoxyethylene sorbitan monolaurate, a drug solution containing 60 mg/L of polyoxyethylene sorbitan monolaurate, Surface tension: 40.8 mN/m) instead of the drug solution of Comparative Example 1.

Comparative Example 6

A prefilled-syringe filled with a POLYSORBATE 80 SOLUTION was obtained in the same manner as Comparative Example 1 except for using POLYSORBATE 80 SOLUTION (available from Wako Pure Chemical Industries, Ltd., polyoxyethylene sorbitan monolate, a drug solution containing 60 mg/L of polyoxyethylene sorbitan monolate, Surface tension: 47.5 mN/m) instead of the drug solution of Comparative Example 1.

Reference Example 1

A 20-mL syringe, to which no lubricants were applied, was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m). The syringe was subjected to high pressure steam sterilization with the gasket closing the barrel. The prefilled syringe of Reference Example 1 was thereby obtained.

Reference Example 2

10 mg of a polydimethylsiloxane (DC360 available from Dow Corning Silicone Co., Ltd., Viscosity at 25° C.: 12,500 c St) was applied to an inner surface of a 20-mL syringe, and the syringe was filled with 20 mL of distilled water (Surface tension: 72.8 mN/m). The syringe was subjected to high pressure steam sterilization with the gasket closing the barrel. The prefilled syringe of Reference Example 2 was thereby obtained.

Reference Example 3

10 mg of a polydimethylsiloxane (DC360 available from Dow Corning Silicone Co., Ltd., Viscosity at 25° C.: 12,500 c St) was applied to an inner surface of a 20-mL syringe, and the syringe was filled with 20 mL of a chondroitin sulfate (chondroitin injection MOHAN 2% available from Mohan Medicine K. K., Surface tension: 70.5 mN/m). The syringe was subjected to high pressure steam sterilization with the gasket closing the barrel. The prefilled syringe of Reference Example 3 was thereby obtained.

(Evaluation of Oil Droplet Generation)

Each of the prefilled syringes obtained in Examples 1 to 11, Comparative Examples 1 to 6, and Reference Examples 1 to 3 was left for 24 hours. Then the formation of oil droplets on the inner surface of the syringe was visually observed. The results are shown in Table 1.

(Measurement of Sliding Friction)

Each of the prefilled syringes produced in Examples 1 to 11, Comparative Examples 1 to 6, and Reference Examples 1 to 3 was left for 24 hours. Then the sliding friction of the gasket in the syringe was measured by a universal testing machine INSTRON 5565 manufactured by Instron Japan Company. The results are shown in Table 1.

TABLE 1

| | Viscosity of silicone oil (cSt) | Amount of silica added | Filled drug solution | Surface tension of drug solution | Oil droplet | Sliding friction |
|---|---|---|---|---|---|---|
| Example 1 | 12,500 | 0.1 | HISHIPHAGEN | 66.0 | ○ | 0.38 |
| Example 2 | 12,500 | 0.5 | HISHIPHAGEN | 66.0 | ○ | 0.18 |
| Example 3 | 12,500 | 1 | HISHIPHAGEN | 66.0 | ○ | 0.26 |
| Example 4 | 12,500 | 5 | HISHIPHAGEN | 66.0 | ○ | 0.31 |
| Example 5 | 12,500 | 10 | HISHIPHAGEN | 66.0 | ○ | 0.35 |
| Example 6 | 12,500 | 20 | HISHIPHAGEN | 66.0 | ○ | 0.65 |
| Example 7 | 100 | 5 | HISHIPHAGEN | 66.0 | ○ | 0.51 |
| Example 8 | 1,000,000 | 5 | HISHIPHAGEN | 66.0 | ○ | 0.96 |
| Example 9 | 12,500 | 5 | MINOPHAGEN | 59.7 | ○ | 0.28 |
| Example 10 | 12,500 | 5 | POLYSORBATE 20 SOLUTION | 40.8 | ○ | 0.25 |
| Example 11 | 12,500 | 5 | POLYSORBATE 80 SOLUTION | 45.7 | ○ | 0.25 |
| Comp. Ex. 1 | 12,500 | 0 | HISHIPHAGEN | 66.0 | X | 1.00 |
| Comp. Ex. 2 | 100 | 0 | HISHIPHAGEN | 66.0 | X | 0.65 |
| Comp. Ex. 3 | 1,000,000 | 0 | HISHIPHAGEN | 66.0 | X | 1.17 |

TABLE 1-continued

|  | Viscosity of silicone oil (cSt) | Amount of silica added | Filled drug solution | Surface tension of drug solution | Oil droplet | Sliding friction |
|---|---|---|---|---|---|---|
| Comp. Ex. 4 | 12,500 | 0 | MINOPHAGEN | 59.7 | X | 1.25 |
| Comp. Ex. 5 | 12,500 | 0 | POLYSORBATE 20 SOLUTION | 40.8 | X | 0.50 |
| Comp. Ex. 6 | 12,500 | 0 | POLYSORBATE 80 SOLUTION | 45.7 | X | 0.64 |
| Ref. Ex. 1 | — | 0 | HISHIPHAGEN | 66.0 | — | 10.11 |
| Ref. Ex. 2 | 12,500 | 0 | Distilled water | 72.8 | ○ | 0.202 |
| Ref. Ex. 3 | 12,500 | 0 | Chondroitin sulfate | 70.5 | ○ | 0.202 |

Example 12

To a polydimethylsiloxane (DC360 available from Dow Corning Silicone Co., Ltd., Viscosity at 25° C.: 12,500 c St), 5.0% by weight of a silica (AEROSIL R976S available from Nippon Aerosil Co., Ltd., Specific surface area: 240 $m^2/g$) and 0.1% by weight of a polyoxyethylene hardened caster oil (EMANON CH60 available from Kao Corporation) were added. The obtained composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a barrel of a 20-mL syringe. Then the syringe was filled with 20 mL of a HISHIPHAGEN injection solution (HISHIPHAGEN-C injection available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Example 12 was thereby obtained.

Example 13

A prefilled-syringe filled with a HISHIPHAGEN injection was obtained in the same manner as Example 12 except for using a lubricant prepared by using 20.0% by weight of the silica and 0.1% by weight of the polyoxyethylene hardened caster oil to polydimethylsiloxane instead of the lubricant of Example 12.

Example 14

A prefilled-syringe filled with a HISHIPHAGEN injection was obtained in the same manner as Example 12 except for using a lubricant prepared by using 5.0% by weight of the silica and 15.0% by weight of the polyoxyethylene hardened caster oil to polydimethylsiloxane instead of the lubricant of Example 12.

Example 15

A prefilled-syringe filled with a HISHIPHAGEN injection was obtained in the same manner as Example 12 except for using a lubricant prepared by using 20.0% by weight of the silica and 15.0% by weight of the polyoxyethylene hardened caster oil to polydimethylsiloxane instead of the lubricant of Example 12.

Example 16

A prefilled-syringe filled with a HISHIPHAGEN injection was obtained in the same manner as Example 12 except for using a lubricant prepared by using 10.0% by weight of the silica and 2.5% by weight of the polyoxyethylene hardened caster oil to polydimethylsiloxane instead of the lubricant of Example 12.

Example 17

A prefilled-syringe filled with a HISHIPHAGEN injection solution was obtained in the same manner as Example 12 except for using a lubricant prepared by using 15.0% by weight of the silica and 5.0% by weight of the polyoxyethylene hardened caster oil to polydimethylsiloxane instead of the lubricant of Example 12.

Example 18

To a polydimethylsiloxane (DC360 available from Dow Corning Silicone Co., Ltd., Viscosity at 25° C.: 1,000 cSt), 10.0% by weight of a silica (AEROSIL R976S available from Nippon Aerosil Co., Ltd., Specific surface area: 240 $m^2/g$) and 2.5% by weight of a polyoxyethylene hardened caster oil (EMANON CH60 available from Kao Corporation) were added. The obtained composition was mixed by a T. K. HOMO MIXER manufactured by Tokushu Kika Kogyo Kabushiki Kaisha, and a semi-transparent liquid of a lubricant was obtained. 10 mg of the lubricant was applied to an inner surface of a barrel of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Example 18 was thereby obtained.

Example 19

A prefilled-syringe filled with a HISHIPHAGEN injection solution was obtained in the same manner as Example 18 except for using a polydimethylsiloxane (KF96 available from Shin-Etsu Chemical Co., Ltd., Viscosity at 25° C.: 1,000,000 cSt) instead of the silicone oil of Example 18.

Example 20

To a polydimethylsiloxane (DC360 available from Dow Corning Silicone Co., Ltd., Viscosity at 25° C.: 12,500 cSt) 10.0% by weight of a silica (AEROSIL R976S available from Nippon Aerosil Co., Ltd., Specific surface area: 240 $m^2/g$) and 2.5% by weight of a polyether-modified silicone (KF945 available from Shin-Etsu Chemical Co., Ltd.) were added. The obtained composition was mixed by a T. K. HOMO MIXER manufactured by Tokushu Kika Kogyo Kabushiki Kaisha, and a semi-transparent liquid lubricant was obtained.

10 mg of the lubricant was applied to an inner surface of a barrel of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Example 20 was thereby obtained.

Example 21

A prefilled-syringe filled with a HISHIPHAGEN injection solution was obtained in the same manner as Example 20 except for using a polyoxyethylene sorbitan monooleate (RHEODOL TW-0106V available from Kao Corporation) instead of the nonionic surfactant of Example 9.

Example 22

To a polydimethylsiloxane (DC360 available from Dow Corning Silicone Co., Ltd., Viscosity at 25° C.: 12,500 cSt), 10.0% by weight of a silica (AEROSIL R976S available from Nippon Aerosil Co., Ltd., Specific surface area: 240 m$^2$/g) and 2.5% by weight of a polyoxyethylene hardened caster oil (EMANON CH60 available from Kao Corporation) were added. The resulting composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a barrel of a 20-mL syringe, and the syringe was filled with 20 mL of a MINOPHAGEN injection solution (STRONGER NEO-MINOPHAGEN C available from Minophagen Pharmaceutical Company, a monoammonium glycyrrhizinate-containing drug solution, Surface tension: 59.7 mN/m) and was subjected to high pressure steam sterilization with the gasket closing the barrel. The prefilled syringe of Example 22 was thereby obtained.

Example 23

A prefilled syringe was produced in the same manner as Example 11 except for using POLYSORBATE 20 SOLUTION (available from Wako Pure Chemical Industries, Ltd., a drug solution containing 60 mg/L of polyoxyethylene sorbitan monolaurate, Surface tension: 40.8 mN/m) instead of the drug solution charged to the syringe of Example 22.

Comparative Example 7

10.0% by weight of a silica (AEROSIL R976S available from Nippon Aerosil Co., Ltd., Specific surface area: 240 m$^2$/g) was added to a polydimethylsiloxane (DC360 available from Dow Corning Silicone Co., Ltd., Viscosity at 25° C.: 12,500 cSt). The resulting composition was mixed by a T. K. HOMO MIXER manufactured by Tokushu Kika Kogyo Kabushiki Kaisha, and a semi-transparent liquid of a lubricant was obtained. 10 mg of the lubricant was applied to an inner surface of a barrel of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Comparative Example 7 was thereby obtained.

Comparative Example 8

2.5% by weight of a polyoxyethylene hardened caster oil (EMANON CH60 available from Kao Corporation) was added to a polydimethylsiloxane (DC360 available from Dow Corning Silicone Co., Ltd., Viscosity at 25° C.: 12,500 cSt). The resulting composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a barrel of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Comparative Example 8 was thereby obtained.

Comparative Example 9

0.0% by weight of a silica (AEROSIL R976S available from Nippon Aerosil Co., Ltd., Specific surface area: 240 m$^2$/g) and 25.0% by weight of a polyoxyethylene hardened caster oil (EMANON CH60 available from Kao Corporation) were added to a polydimethylsiloxane (DC360 available from Dow Corning Silicone Co., Ltd., Viscosity at 25° C.: 12,500 cSt) 1. The resulting composition was mixed by a T. K. HOMO MIXER manufactured by Tokushu Kika Kogyo Kabushiki Kaisha, and a semi-transparent liquid lubricant was obtained. 10 mg of the lubricant was applied to an inner surface of a barrel of a 20-mL syringe, and the syringe was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m) and was subjected to high pressure steam sterilization with the gasket closing the barrel. The prefilled syringe of Comparative Example 9 was thereby obtained.

Comparative Example 10

A prefilled-syringe filled with a HISHIPHAGEN injection solution was obtained in the same manner as Comparative Example 9 except for using a lubricant prepared by adding 1.0% by weight of the silica and 2.5% by weight of the polyoxyethylene hardened caster oil to the polydimethylsiloxane instead of the lubricant of Comparative Example 9.

Comparative Example 11

A prefilled-syringe filled with a HISHIPHAGEN injection solution was obtained in the same manner as Comparative Example 9 except for using a lubricant prepared by adding 30.0% by weight of the silica and 2.5% by weight of the polyoxyethylene hardened caster oil to the polydimethylsiloxane instead of the lubricant of Comparative Example 9.

Reference Example 4

A 20-mL syringe, to which no lubricants were applied, was filled with 20 mL of a HISHIPHAGEN injection solution (HISHIPHAGEN-C injection solution available from Nipro Pharma Corporation, a monoammonium glycyrrhizinate-containing drug solution, Surface tension: 66 mN/m). The syringe was subjected to high pressure steam sterilization with the gasket closing the barrel. The prefilled syringe of Reference Example 4 was thereby obtained.

Reference Example 5

10 mg of a polydimethylsiloxane (DC360 available from Dow Corning Silicone Co., Ltd., Viscosity at 25° C.: 12,500 cSt) was applied to an inner surface of an outer cylinder of a 20-mL syringe, and the syringe was filled with 20 mL of distilled water (Surface tension: 72.8 mN/m). The syringe was subjected to high pressure steam sterilization with the gasket closing the barrel. The prefilled syringe of Reference Example 5 was thereby obtained.

Reference Example 6

10 mg of a polydimethylsiloxane (DC360 available from Dow Corning Silicone Co., Ltd., Viscosity at 25° C.: 12,500 cSt) was applied to an inner surface of an outer cylinder of a 20-mL syringe, and the syringe was filled with 20 mL of a chondroitin sulfate (chondroitin injection MOHAN 2% available from Mohan Medicine K. K., Surface tension: 70.5 mN/m). The syringe was subjected to high pressure steam sterilization with the gasket closing the barrel. The prefilled syringe of Reference Example 6 was thereby obtained.

(Evaluation of Suspended Oil Droplet)

Each of the prefilled syringes produced in Examples 12 to 23, Comparative Examples 7 to 11, and Reference Examples 4 to 6 was left for 24 hours and shaken by a flask shaker for 10 minutes at a rate of 100 times per minute. The formation of oil droplets in the syringe inner surface and the drug solution was visually observed. The results are shown in Table 2.

(Measurement of Sliding Friction)

Each of the prefilled syringes produced in Examples 12 to 23, Comparative Examples 7 to 11, and Reference Examples 4 to 6 was left for 24 hours, and the sliding friction of the gasket in the syringe was measured by a universal testing machine INSTRON 5565 manufactured by Instron Japan Company.

The results are shown in Table 2.

TABLE 2

| | Viscosity of straight silicone oil (cSt) | Content of silica (% by weight) | Nonionic surfactant | | Drug | Suspended oil droplet | Sliding friction (kgf) |
| --- | --- | --- | --- | --- | --- | --- | --- |
| | | | Agent | Content (% by weight) | | | |
| Example 12 | 12,500 | 5.0 | EMANON | 0.1 | HISHIPHAGEN | None | 0.28 |
| Example 13 | 12,500 | 20.0 | EMANON | 0.1 | HISHIPHAGEN | None | 0.71 |
| Example 14 | 12,500 | 5.0 | EMANON | 15.0 | HISHIPHAGEN | None | 0.22 |
| Example 15 | 12,500 | 20.0 | EMANON | 15.0 | HISHIPHAGEN | None | 0.62 |
| Example 16 | 12,500 | 10.0 | EMANON | 2.5 | HISHIPHAGEN | None | 0.37 |
| Example 17 | 12,500 | 15.0 | EMANON | 5.0 | HISHIPHAGEN | None | 0.55 |
| Example 18 | 1,000 | 10.0 | EMANON | 2.5 | HISHIPHAGEN | None | 0.27 |
| Example 19 | 1,000,000 | 10.0 | EMANON | 2.5 | HISHIPHAGEN | None | 0.87 |
| Example 20 | 12,500 | 10.0 | KF945 | 2.5 | HISHIPHAGEN | None | 0.29 |
| Example 21 | 12,500 | 10.0 | RHEODOLTW | 2.5 | HISHIPHAGEN | None | 0.32 |
| Example 22 | 12,500 | 10.0 | EMANON | 2.5 | MINOPHAGEN | None | 0.31 |
| Example 23 | 12,500 | 10.0 | EMANON | 2.5 | POLYSORBATE 20 | None | 0.30 |
| Comp. Ex. 7 | 12,500 | 10.0 | — | 0 | HISHIPHAGEN | Observed | 0.30 |
| Comp. Ex. 8 | 12,500 | 0 | EMANON | 2.5 | HISHIPHAGEN | Observed | 1.31 |
| Comp. Ex. 9 | 12,500 | 10.0 | EMANON | 25.0 | HISHIPHAGEN | Observed | 0.26 |
| Comp. Ex. 10 | 12,500 | 1.0 | EMANON | 2.5 | HISHIPHAGEN | Observed | 0.23 |
| Comp. Ex. 11 | 12,500 | 30.0 | EMANON | 2.5 | HISHIPHAGEN | Observed | 1.89 |
| Ref. Ex. 4 | — | 0 | — | 0 | HISHIPHAGEN | None | 10.11 |
| Ref. Ex. 5 | 12,500 | 0 | — | 0 | Distilled water | None | 0.20 |
| Ref. Ex. 6 | 12,500 | 0 | — | 0 | Chondroitin sulfate | None | 0.20 |

As is clear from Table 1, the syringes of the present invention (Examples 1 to 11), which were coated with the lubricants containing a silicone oil and a fine silica powder, did not form oil droplets on the inner surface even in the case of being filled with the drug solutions containing the surface-active drugs, in the same manner as Reference Examples 2 and 3 using drug solutions with no surface activity. On the other hand, the syringes coated with the conventional lubricants composed of only the silicone oils (Comparative Examples 1 to 6) formed oil droplets on the surface when they were filled with the drug solutions containing the surface-active drugs.

Further, as is clear from Table 1, in the syringes of the invention (Examples 1 to 11), which were coated with the lubricants containing a silicone oil and a fine silica powder, the sliding frictions of the gaskets were hardly increased or increased only slightly to values sufficiently lower than that of the syringe of Reference Example 1 without a lubricant coating even in the case of being filled with the drug solutions containing the surface-active drugs. On the other hand, in the syringes coated with the conventional lubricants composed of only the silicone oils (Comparative Examples 1 to 6), in the case of being filled with the drug solutions containing the surface-active drugs, the sliding frictions of the gaskets were relatively increased to higher values as compared with those of Examples using the same silicones.

As is clear from Table 2, the syringes of Examples 11 to 23, which were coated with the lubricants of the invention comprising the silicone oil, predetermined amounts of a fine silica powder and a nonionic surfactant, did not form oil droplets in the syringe inner surfaces or the drug solutions by shaking, and the sliding frictions of the gaskets in the syringe were prevented from increasing. In addition, the formation of oil droplets without shaking is not observed in Examples 12 to 23 by an evaluation in the same manner of "Evaluation of oil droplet generation".

Further, as is clear from Table 2, in the syringes of Examples 11 to 23, which were coated with the lubricants of the invention, even in the case of filling with the drug solutions containing the surface-active drugs, the sliding frictions of the gaskets were hardly increased as compared with the conventional syringes of Reference Examples 5 and 6 filled with the drug solutions with no surface activity, and the sliding frictions were increased only slightly to values sufficiently lower than that of the syringe of Reference Example 4 without a lubricant coating. On the other hand, in the syringes of Comparative Examples 8, 10, and 11, which were coated with the lubricants having contents of a fine silica powder without the range according to the invention, in the case of filling with the drug solutions containing the surface-active drugs, the sliding frictions of the gaskets were higher.

It is clear from the Examples that the syringe according to the invention, coated with the lubricant containing the silicone oil and the fine silica powder, can prevent the formation of the oil droplets and an increase of the gasket sliding friction as compared with syringes coated with the conventional lubricants composed of only the silicone oil.

The invention claimed is:

1. A syringe comprising:
   a barrel,
   a gasket contacting tightly with an inner surface of the barrel,
   a plunger extending from the gasket to a rear end of the syringe for sliding the gasket in the barrel, the inner surface of the barrel being coated with a lubricant containing a straight silicone oil as a main component, a fine silica powder, and a nonionic surfactant, the lubricant containing 5 to 20% by weight of the fine silica powder and 0.1 to 15% by weight of the nonionic surfactant, and
   the syringe being adapted to inject a drug solution containing a drug having a surface activity.

2. The syringe according to claim 1, wherein the silicone oil contained in the lubricant has a viscosity of 100 to 1,000,000 cst at 25° C.

3. The syringe according to claim 1, wherein the fine silica powder contained in the lubricant has a specific surface area of 100 m2/g or more.

4. The syringe according to claim 1, wherein the nonionic surfactant comprises at least one agent selected from the group consisting of polyoxyethylene higher alcohol ethers, polyoxyethylene alkyl phenyl ethers, sorbitan alkylates, polyoxyethylene sorbitan alkylates, glycerolalkylates, polyoxyethylene hardened caster oils, and silicone-based nonionic surfactants having hydrophilic substituents.

5. The syringe according to claim 4, wherein the nonionic surfactant comprises at least one agent selected from the group consisting of polyoxyethylene sorbitan monooleate, polyoxyethylene hardened caster oils, and polyether-modified silicones.

6. A prefilled syringe comprising:
   a barrel,
   a gasket contacting tightly with an inner surface of the barrel,
   a plunger extending from the gasket to a rear end of the syringe for sliding the gasket in the barrel, the inner surface of the barrel being coated with a lubricant containing a straight silicone oil as a main component, a fine silica powder, and a nonionic surfactant, the lubricant containing 5 to 20% by weight of the fine silica powder and 0.1 to 15% by weight of the nonionic surfactant, and
   the syringe being filled with a drug solution containing a drug having a surface activity.

7. The syringe according to claim 6, wherein the drug having a surface activity has a surface tension of 70 mN/m or less.

8. The syringe according to claim 7, wherein the drug having a surface activity comprises at least one agent selected from the group consisting of hyaluronate salts, glycyrrhizinate salts, polyoxyethylene sorbitan esters, polyethylene glycol, polyoxyethylene castor oil, polypropylene glycol, lecithin, arid glycerin.

* * * * *